United States Patent
Joshi (10) Patent No.: US 9,884,024 B2
(45) Date of Patent: *Feb. 6, 2018

(54) PHYSICALLY DISPERSED, MOLECULARLY DISSOLVED AND/OR CHEMICALLY BOUND DRUG(S) IN AN EMPTY, HARD CAPSULE SHELL COMPOSITION

(71) Applicant: Hemant N Joshi, Parsippany, NJ (US)

(72) Inventor: Hemant N Joshi, Parsippany, NJ (US)

(*) Notice: Subject to any disclaimer, the term of this patent is extended or adjusted under 35 U.S.C. 154(b) by 5 days.

This patent is subject to a terminal disclaimer.

(21) Appl. No.: 14/280,677

(22) Filed: May 19, 2014

(65) Prior Publication Data

US 2015/0328164 A1    Nov. 19, 2015

Related U.S. Application Data (63) Continuation-in-part of application No. 12/841,008, filed on Jul. 21, 2010, now Pat. No. 8,728,521, which is a continuation of application No. 11/306,398, filed on Dec. 27, 2005, now abandoned.

(51) Int. Cl.
*A61K 9/48* (2006.01)

(52) U.S. Cl.
CPC .............. *A61K 9/4858* (2013.01); *A61K 9/48* (2013.01); *A61K 9/4891* (2013.01)

(58) Field of Classification Search
None
See application file for complete search history.

(56) References Cited

U.S. PATENT DOCUMENTS

| | | | | |
|---|---|---|---|---|
| 4,247,702 A | * | 1/1981 | Felsch | A61K 9/4858 |
| | | | | 548/146 |
| 5,264,223 A | | 11/1993 | Yamamoto et al. | |
| 5,756,123 A | * | 5/1998 | Yamamoto | A61K 9/4816 |
| | | | | 424/451 |

(Continued)

FOREIGN PATENT DOCUMENTS

EP    2178533 B1 *  3/2013    ........... A61K 31/731

OTHER PUBLICATIONS

Gonzalez et al., Polysaccharides as Antiviral Agents: Antiviral Activity of Carrageenan, Antimicrobial Agents and Chemotherapy, Sep. 1987, vol. 31, No. 9, p. 1388-1393.*

(Continued)

*Primary Examiner* — Carlos A Azpuru
*Assistant Examiner* — Casey S Hagopian
(74) *Attorney, Agent, or Firm* — Hooker & Habib, P.C.

(57) ABSTRACT

The present invention proposes a design to incorporate drug(s) in the hard capsule shells (body and cap) composition. Drug(s) in the cap and body of the capsule shell may be the same or may be different. Other drug(s) in the form of granules, beads etc. can be filled into the capsules as a core material. The drug(s) in the capsule core material may be the same as in the shell-composition or may be different. Thus, the same capsule may contain different drug(s) as the core material and in the shell. The key advantages of incorporation of drug in the capsule shell compositions are to minimize drug-drug interaction and to obtain a desired rate of release of the drug(s), mainly for potent ones. The concept can be applied to the hard gelatin, and hard non-gelatin capsules.

20 Claims, 2 Drawing Sheets

(56) References Cited

U.S. PATENT DOCUMENTS

| | | | | |
|---|---|---|---|---|
| 6,410,524 B1* | 6/2002 | Perez | ................... | A61K 31/585 |
| | | | | 514/175 |
| 8,728,521 B2* | 5/2014 | Joshi | ................... | A61K 9/4808 |
| | | | | 424/464 |
| 2007/0148227 A1* | 6/2007 | Joshi | ................... | A61K 9/4808 |
| | | | | 424/451 |
| 2010/0285116 A1* | 11/2010 | Joshi | ................... | A61K 9/4808 |
| | | | | 424/453 |

OTHER PUBLICATIONS

Eccles et al., Efficacy and Safety of an antiviral Iota-Carragennan nasal spray: a randomized double-blind, placebo-controlled exploratory study in volunteers with early symptoms of the common cold, Respiratory Research, Aug. 2010, 11 (108), p. 1-10.*

Abstract only, Myra L. Weiner, Food Additive Carrageenan: Part II: A Critical Review of Carrageenan in vivo Safety Studies, Critical Reviews in Toxicology, vol. 14, issue 3, pp. 244-269 (2014).

CP Kelco ApS, GENU Carrageenan Book, 28 pages.

* cited by examiner

PHYSICALLY DISPERSED, MOLECULARLY DISSOLVED AND/OR CHEMICALLY BOUND DRUG(S) IN AN EMPTY, HARD CAPSULE SHELL COMPOSITION

RELATED APPLICATIONS

This patent application claims the benefit of U.S. patent application Ser. No. 12/841,008 filed on Jul. 21, 2010 and titled, "Physically/molecularly distributed and/or chemically bound medicaments in empty, hard capsule shells". The current application is a Continuation application of the previous application U.S. patent application Ser. No. 12/841,008 filed on Jul. 21, 2010 and it seeks broader claim coverage. U.S. patent application Ser. No. 12/841,008 will be issued as a U.S. Pat. No. 8,728,521. U.S. patent application Ser. No. 12/841,008 is a continuation of U.S. patent application Ser. No. 11/306,398 filed on Dec. 27, 2005 and titled, "Physically/molecularly distributed and/or chemically bound medicaments in capsule shells"

BACKGROUND OF THE INVENTION

Field of Invention

The Present invention relates to an improved or modified capsule shell, which is commonly used as a drug delivery system.

Description of the Related Art

A drug is "a chemical substance used in the treatment, cure, prevention, or diagnosis of disease or used to otherwise enhance physical or mental well-being. Medicament is a medicine or a substance used in a therapy. In this patent application, the terms "drug" and "medicament" have been used interchangeably. A combination drug therapy has been gaining a lot of importance in recent times. The combination therapy in medicine involves administration of two or more therapeutically active ingredients. The active ingredient may be administered in a single dosage form or each active ingredient may be administered separately. The reasons of a combination therapy could be multiple—synergistic effects of drugs, reduction of side effect of the primary drug by an adjunct drug, avoidance of taking multiple tablets/capsules per day thereby savings on co-payment for different medicines and assurance of patient compliance to drug therapies. In some embodiments of the combination drug therapy, the active ingredients are administered in a single dosage form. In those instances, it is important to show that different drugs combined in the same dosage form are stable during storage of the dosage form and should not interact physically or chemically with other drugs or excipients to produce degradation products. Also, each drug should show the desired release rate from the dosage form to get absorbed in sufficient quantities upon oral administration or release the drug to surrounding environment in case of other delivery routes.

Pharmaceutical capsule dosage forms are widely used in delivering drugs. Composition is the combination of parts or elements and it is the way in which something is put together. The composition of the capsule shell consists of a list of ingredients incorporated and their respective quantities. The main two types of capsules are—hard shell capsules and soft shell capsules. The present patent relates to the hard capsule shell composition. The capsules are normally prepared using gelatin and other excipients. In recent times, several polymers have been employed to manufacture hard shell capsules. In 1977, Christen and Cheng patented (U.S. Pat. No. 4,026,986) hard shell capsules manufactured using 2-hydroxyalkyl starch. It facilitated the production of shells and produced improved shells. WO 1997004755 (International application #: PCT/EP1996/003263) prepared hard gelatin capsules with internal or external polymer coating using the double dipping technique. The inventors used polyvinyl alcohol and polyvinyl acetate polymers along with necessary additives. Gennadios invented non-gelatin capsules (U.S. Pat. No. 6,214,376) comprising k-carrageenan, water soluble plasticizer, and dextrins. The composition also included hydrolyzed starch as a variation. U.S. Pat. No. 6,517,865 claimed hard and soft capsules comprising of water soluble cellulose ethers, hydrocolloids and sequestering agents. The capsules also comprised of a coating with polymers including cellulose acetate phthalate, hydromellose phthalate etc. In 2004 patent by Chen et al. (U.S. Pat. No. 6,752,953), authors described the usage of other polymers such as cellulose derivatives including cellulose, cellulose ester, methylcellulose, hydroxypropyl methyl cellulose etc., acrylates including polyacrylate, polymethylacrylate, poly(methacrylate-methylmethacrylate) etc., and polyolefins including polyethylene, polypropylene, polyvinyl chloride, polyvinyl alcohol etc. to prepare capsules. The inventors described a heat-melting method to prepare the capsule shells. U.S. Pat. No. 8,029,821 used low-substituted cellulose ether to produce hard capsules. The inventors also proposed a method for capsule preparation. The pins were dipped in the alkaline solution of low-substituted cellulose ether followed by dipping in an aqueous acid solution to form a gel (low-substituted cellulose ethers are soluble in alkaline medium and form a gel in the acidic environment). The pins covered with the gel were further washed with water before the drying step. U.S. Pat. No. 6,949,256 used a mixture of kappa carrageenan and iota carrageenan. Kappa carrageenan is known to form a strong gel in the presence of potassium cations. However, these tend to be brittle and exhibit syneresis (exudating of liquid portion of the gel). Iota carrageenan reacted with calcium cations and formed a weaker and more flexible gel. In the U.S. Pat. No. 8,105,625, Rajewski and Haslam prepared hard shell capsules with pullulan, a plasticizer and a dissolution enhancing agent. The capsules were meant to dissolve in the mouth cavity (orally dissolving capsules). US patent application #2008/0274187 prepared hard capsule compositions comprising carrageenan, locust bean gum, xanthan gum, sorbitol, and pullulan. These capsules eliminated the problem of cracking, embrittlement, chipping and deformation due to water loss and mechanical stress. US patent application #2010/0168410 described a composition of hard capsules of hydroxypropyl methylcellulose and the process of dip-coating manufacture. The dipping pins were heated at 55-95° C. and the polymer solution was maintained at 1 to 10° C. below its gelling temperature.

McConville et al. (Eur. J. Pharmaceutics & Biopharm. 57: 541-549 (2004)) prepared a capsule filled with low-substituted hydroxypropyl cellulose in which a propanol tablet was placed followed by an erodible tablet containing HPMC and lactose manufactured by either direct and wet granulation technique. In this case, the body of the capsule was pre-coated with insoluble ethyl cellulose suggesting the drug release only after the dissolution of the cap of the capsule. In this case, the capsule shell was not loaded with the drug—propranolol.

In the US patent application #2004/0146559, a film was formed on the inner surface of the capsule shell. The shell may have different properties to alter the drug release rates. In this patent, the core and the shell were manufactured in situ. In the present invention, the empty hard capsule shell composition containing the drug is produced by the manufacturers of empty capsules (such as, Capsugel, Universal capsules, and Shionogi capsules).

In the U.S. Pat. No. 6,709,427, microspheres were encapsulated to produce microcapsules. The core technology was to prepare microspheres. Microcapsule is a totally different kind of drug delivery technique compared to the hard capsule shell dosage form. In the hard capsule shell dosage form, the drug granules or powder or microspheres are filled in the capsule shell body on which the cap is fitted.

In the US patent application #2003/0104062, the capsules core was loaded with the drug. The "capsule core" is the empty space within the capsule shells and not the capsule shell composition. The shell surrounding the drug-containing core governs the release rate (zero order) of the drug by diffusion mechanism due to its swelling. The shell also promoted gastric retention of the capsules by swelling upon the imbibition of gastric fluid to a size that was retained in the stomach during the fed mode. In the US patent application #2003/0104062, no drug was incorporated in the capsule shell composition. In another embodiment, the drug was incorporated in the shell so as to produce a burst effect. In this case, the same drug is incorporated in the core and in the shell/casing. In this patent, the preparation of capsule shell was part of the manufacturing process in situ. The desired zero order release, the manufacturing process and drug combination are the key differences between US patent application #2003/0104062 and the current patent application.

U.S. Pat. No. 7,666,398 by Uhrich K described the composition and method of preparation of a polymeric drug delivery system using polyanhydrides. Polyanhydrides linked low molecular weight drugs containing a carboxylic acid group and an amine, thiol, alcohol or phenol group within their structure. The inventors did not disclose the capsule as the drug delivery system.

Yamamoto et al. in their U.S. Pat. No. 5,756,123 described a capsule shell comprising of hydropropyl methylcelluse (HPMC), carrageenan as a gelling agent and calcium or potassium ions as the co-gelling agent. Carrageenan helped to improve the shapability of HPMC. Co-gelling agents assisted the gelation of carrageenan. Calcium ions were used for iota-carrageenan whereas potassium ions were used for kappa carrageenan. Carrageenan was not included in this composition as a therapeutically active agent. But it was used as a gelling agent to improve capsule properties.

Sakanishi et al in their US patent application #2006/0275361 described rapidly dissolving gelatin compositions. Although gelatin is water-soluble, it takes several minutes to dissolve in mouth to release their core material. The inventors added dissolution enhancing materials to the gelatin composition such as polyol plasticizer and water-insoluble particulate components. Polyols were selected from the group consisting of glycerin, propylene glycol, sorbitol, maltitol, xylitol, mannitol, erythritol, isomalt, lactitol and combinations thereof. One has to be very careful about understanding the definitions of "capsule shell-forming composition" and "core composition" Gelatin, polyol and water-insoluble component formed a "capsule shell-forming composition" with which, the capsules were formed. The "core composition" was the one which was filled in the above-mentioned capsules. The "core composition" may include sweeteners, flavors, medicaments and other excipients. The patent quoted, "Core materials may include hydrophobic components, such as flavor oils or vegetable oils, as well as hydrophilic component". Anyone knowledgeable in the preparation of making capsules will agree that oils are not preferred in the "capsule shell-0forming composition".

The patent further quoted, "The core compositions, as previously mentioned, may take a variety of physical forms, such as powders, granules, gels, pastes or liquids". It was clear that the inventors intended to fill their rapidly dissolving gelatin capsules with the "core materials" prepared using the core composition, which included active medicaments. The inventors did not intend to add the "actives" in the "capsule shell-forming composition". Also, the inventors did not teach to make capsules using polymeric materials such as HPMC (hydroxypropyl methylcellulose).

There are mainly two methods to prepare capsules: pin dip-coating and heat-melting. A liquid mass is produced by dissolving the capsule shell-forming compositions in a solvent system or by melting at an appropriate temperature. In the dip-method, plurality of pins maintained at a certain temperature is dipped in the solution and is withdrawn at a pre-determined rate while spinning. The pins coated with capsule composition are then dried at a gradual rate. The capsules (body and cap) are separated from the pins and are trimmed to an exact length. The method has been employed to prepare the body and cap of the capsules. The body and cap are joined or fitted together or cooperatively engaged and a logo is printed, if necessary.

InnerCap (http://www.innercap.com/) proposed combination capsules in which a capsule may contain another small capsule or a tablet along with granules (multiphase, multi-compartment capsule technology). The granules may be made up of beads or other forms, which may contain more than one type of drugs. This way, more than one type of drug may be combined in the same capsule. This is a different technology compared to the current patent application.

Soft gelatin capsules are another form of capsules in which a liquid core material is filled. It has created a niche market of its own in the drug delivery technology. In coming times, soft non-gelatin may be introduced in the market due to advent of new polymeric systems.

BRIEF DESCRIPTION OF FIGURES

FIG. 1 also shows the drug-loading in the capsule cap. FIG. 1 shows loading of a single drug. But more than one drug can be loaded in the capsule shell too.

SUMMARY OF THE INVENTION

The following are the key words used and the definition of various terms applicable to this patent application.

The present invention proposes a design to incorporate drug(s) in the capsule shell-forming composition (body and cap). The term "drug(s)" is optionally plural. It means one or more drugs may be incorporated in the capsule shell-forming composition. Drugs in the compositions of cap and body of the capsules may be the same or may be different. Other medicaments in the form of granules, beads etc. can be filled in the capsules, which are termed as "core materials". Thus, the same capsule may contain drugs in the core matrix and in the capsule shell composition.

There are two key phrases—"capsule shell-forming composition" and "capsule-core material/formulation".

Capsule shell-forming composition described herein includes a composition suitable for forming empty hard shell capsules. Capsule shell-forming composition in this patent application comprises of gelatin or a suitable polymer or a mixture of polymers, and suitable excipients including plasticizer, coloring agent etc. The term "comprising" or "comprises" is synonymous with "including", "containing" and "characterized by", is inclusive or open-ended. In some embodiments, drug/drugs may be added to the capsule shell-forming composition. The capsule shell-forming compositions may be different for capsule cap and capsule body.

An "excipient" as used herein is more or less an inert substance added as diluents or vehicles or to give form or consistency or properties. Excipients may also act as a preservative. A "preservative" is understood herein to mean certain embodiments which are substances added to inhibit chemical change or microbial growth. When the preservative inhibits microbial growth, such preservatives may include, but are not limited to sodium benzoate, methylparaben, propyl gallate BP, sorbic acid, chlorobutanol, dihydroacetic acid, monothioglycerol, potassium benzoate, propylparaben, benzoic acid, benzalkonium chloride, benzethonium chloride, benzyl alcohol, butylparaben, cetylpyridinium chloride, ethylenediamine, ethylparaben, thimerosal and potassium sorbate.

In certain embodiments, the capsule shell-forming composition may also contain an antioxidant. An "antioxidant" is understood herein to mean certain embodiments which are substances that inhibit oxidation. Such antioxidants include, but are not limited to, asocorbyl palmitate, butylated hydroxyanisole, butylated hydroxytoluene, potassium metabisulfite, and sodium metabisulfite.

In certain embodiments, the capsule shell-forming composition may also contain a flavoring agent. A "flavoring agent" is understood herein to mean certain embodiments which are substances that alter the flavor of the composition during oral consumption. A type of "flavoring agent" would be a sweetener. Preferred sweeteners can be natural or artificial. Flavoring agents can be chosen from a group commonly used in the pharmaceutical dosage forms.

In certain embodiments, the capsule shell-forming composition may also contain a buffering agent. A "buffering agent" is a weak acid or a weak base or a mixture of two, which helps to prevent fluctuations in the pH of the medium when exposed to an acidic or basic environment. Some of the examples of "buffering agents" may be, but not limited to, phosphate, citrate, borate and acetate.

Figure 2:
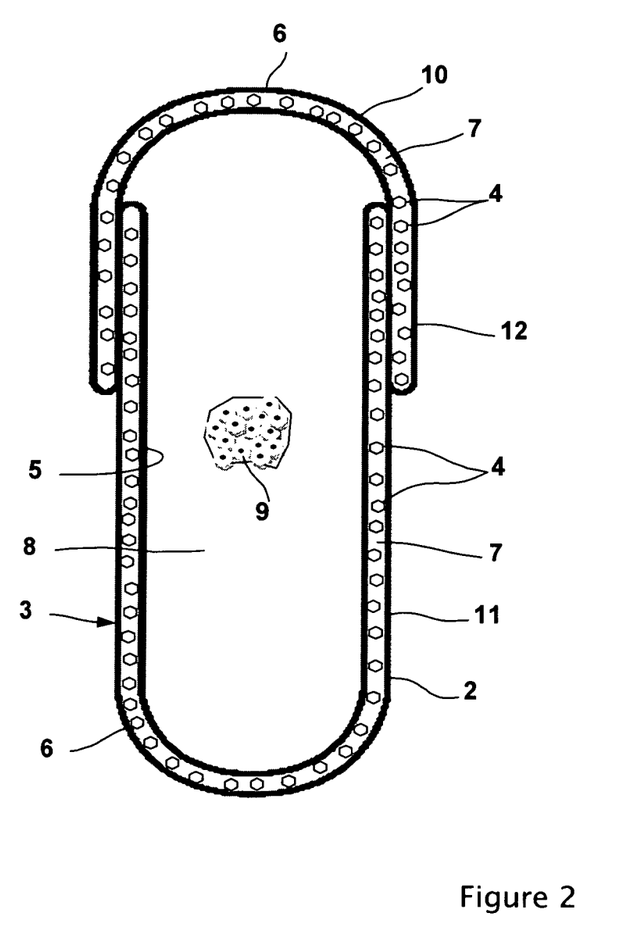
FIG. 2 depicts a hard shell capsule in which the capsule cap is cooperatively engaged in the capsule body. In this figure, both the capsule cap and body compositions are loaded with a drug. It also shows the "core material" of the capsule, which contains a second drug filled into the capsule.

A "Capsule dosage form" defined here as a delivery system for a drug(s) prepared with suitable materials such as gelatin or polymers to form a capsule shell and has a shape as depicted in FIG. 2.

A "capsule shell" is referred to as a film-forming composition used to encapsulate an active moiety in a capsule dosage form. For this patent, the capsule shell-forming composition also contains a drug or drugs.

A "medicament" is an agent that promotes recovery from an ailment or an injury. Similar words to medicament are medicine, drugs, therapeutic agent and an active moiety.

The "therapeutically effective amount" is the amount of pharmaceutical or nutraceutical substance that treats, totally or partially, a disease state or alleviates one or more symptoms of the condition.

The "empty, hard shell capsule" as name suggests is hard, durable and smooth capsule. It retains its shape and it is dry in nature. As evident from the word "empty", there is nothing inside core portion of the capsule shell when supplied by the capsule manufacturing company. Currently such "empty, hard shell capsule" compositions available in the market do not contain any drug(s). The hard capsule shell comprises of two parts—a body in the core of which holds the contents of the dosage form ("capsule core formulation or capsule core material"), such as, powders/granules/beads/a tablet/a capsule and a cap, which fits on the body of the capsule shell and acts as a cover (U.S. Pat. Nos. 4,510,168 and 4,532,881). The "capsule core material" may be prepared from a wide variety of materials including, but not limited to, sweetners, flavors, medicaments, coloring agents, dispersing agents, lubricants and glidants etc. The "capsule core material" can be in the form of but not limited to powder, granules, beads, pellets, microspheres, microcapsules, mini-tablets and mini-capsules. Someone may argue that the body is type of a core. However, people working in the field of pharmaceutical formulations will not confuse the "body" of the capsule shell with the material within the core of the capsule.

The "drug-loaded empty, hard shells capsules" means the empty, hard capsule shells in which a drug is loaded in the shell composition. The term "loaded" means the drug is either physically dispersed or molecularly dissolved in the shell composition or chemically bound to the polymeric material incorporated in the capsule shell-forming composition. The term "physically dispersed" in the above sentence means, the drug is suspended as a powder, crystals or granules in the capsule shell-forming composition. In other words, drug(s) is in an insoluble form in the capsule-shell forming composition. The term "molecularly dissolved" in the above sentence means, the drug(s) is dissolved molecularly in the capsule shell-forming composition. Undissolved particles less than 200 nm particle size are not visible to the necked eyes and can be considered "dissolved". The term "chemically bound to the polymeric material" in the above sentence means, the drug is ion-paired or complexed or covalently bound to the gelatin or polymer used to form the capsule shell. These drug-loaded empty hard shell capsules are prepared by incorporating drug in the capsule shell-forming composition, which is then converted to a capsule shape (body and cap).

The key advantage of incorporation of drug(s) in the shell is to obtain a desired rate of release of the medicament, mainly for potent drugs. The rate of release will be controlled by the way in which the drug is embedded in the capsule shell-forming composition. Other advantage is to produce a combination drug delivery system. The concept can be used for the hard gelatin, hard non-gelatin, soft gelatin and soft non-gelatin capsules. The type of medicaments or drugs embedded in the capsule shell-forming composition can be from any therapeutic class, but should be of low-dose. The term "low-dose" is relative and in general, for the purpose of this patent, it may be less than 50 mg of dose. The drug has to be stable in the capsule shell during manufacture and during appropriate storage conditions for the capsules.

Figure 1:
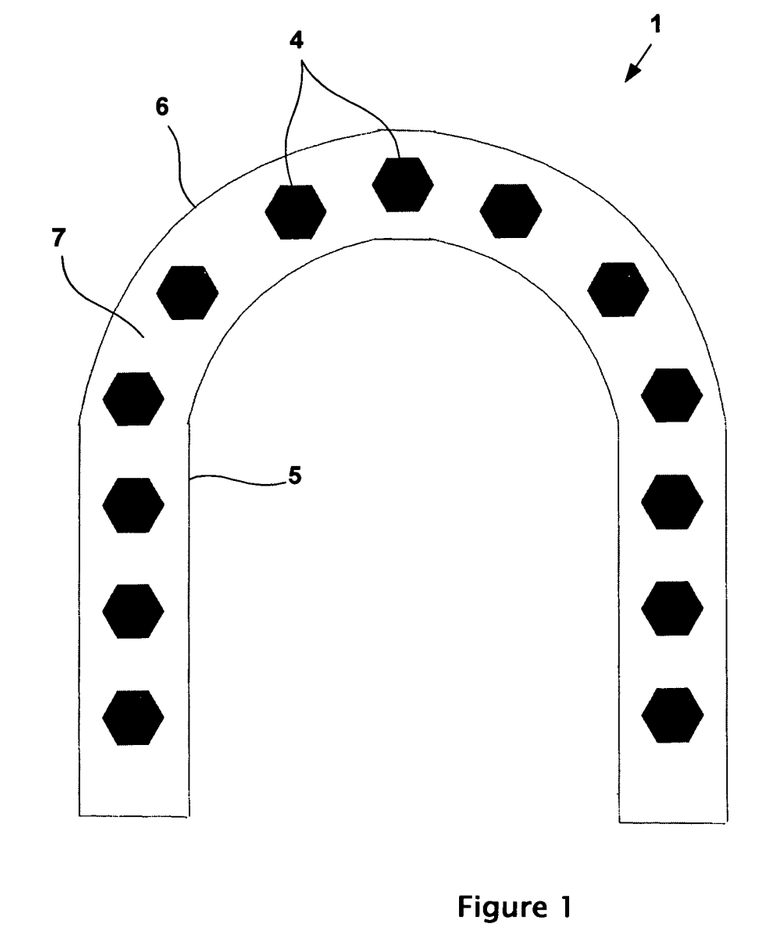
FIG. 1 depicts a capsule cap which cooperatively engages in the capsule body to form a hard shell capsule.

In accordance with the present invention, FIG. 1 depicts a Capsule Cap 1 that cooperatively engages a Capsule Body 2 to form a Hard shell capsule 3 (see FIG. 2). The Capsule Cap 1 in FIG. 1 has Medicament or Drug Molecules 4 dispersed throughout between a Capsule Cap inner surface 5 and a Capsule cap outer surface 6. The Capsule Body 2 in the illustrated embodiment of the hard shell Capsule 3 has a similar structure, that is, a drug dispersed throughout the Capsule Body 2 between inner and outer surfaces of the Capsule Body 2. The Shell Composition 7 of the Capsule Cap 1 or the Capsule Body 2 may consist of gelatin, HPMC, cellulose-derivatives, acrylates, polyolefins, vinyl polymers and other polymeric systems used in forming Caps and Body of conventional hard shell capsules. The main constituent of the composition 7 of the capsule shell (body or cap) may also be a combination of polymers mentioned above. The Shell Composition 7 (body or cap) may also contain other excipients such as plasticizers, emulsifiers, stabilizers, colorants, cross-linking agents etc. The rate of dissolution of capsule shell in a desired media or location within the body may be altered using appropriate capsule shell composition 7 as it is known in the art. The Medicament or Drug 4 can be physically dispersed (insoluble form) or molecularly dissolved (soluble form) throughout the Shell Composition 7 of the Capsule Cap 1 or Body 2. Capsule core is depicted in FIG. 2 as 8. The Capsule Core 8 is filled with Capsule Core Material 9. The Capsule core material 9 may contain a drug or a combination of drugs along with excipients. The Outer Surface of Capsule Cap 6 can be coated with 10 and the Outer Surface of Body can be coated with 11. In some embodiments, the coating materials 10 and 11 may be the same and in some cases, the coatings 10 and 11 may be different. In some cases, there may not be any coatings 10 or 11. At the region where the Capsule Cap 1 fits on the Capsule body 2, in some embodiments, a Band 12 is placed to seal the gap.

In the present invention proposes a new way of combining more than one drug component in the capsule formulation. It may serve two purposes—prevent/reduce drug-drug interaction during storage of the dosage form and the release rate of each drug may be controlled to a desired value. The drug-loaded empty hard capsule shells, in which the active ingredient is physically dispersed or molecularly dissolved or chemically bound in the capsule shell, are then used further to manufacture pharmaceutical capsule formulations by filling them with drug-loaded powder, granules, beads, etc., i.e., the capsule core materials. In one embodiment, the drug is dissolved in the capsule shell-forming composition. In another embodiment, the drug which is insoluble in the Capsule Shell-forming composition is physically dispersed or suspended. In another embodiment, the drug may be partially dissolved and partially suspended in the capsule shell-forming composition. For the purpose of this patent application, partially is defined as more than 10% of the total drug amount. For example, 30% drug may be physically dispersed and 70% drug may be in the molecularly dissolved form. In yet another embodiment, the drug is chemically bound to the gelatin or polymer used in the Capsule shell-forming composition. In yet another embodiment, the drug is chemically bound to the gelatin or polymer used in the capsule shell-forming composition and also dissolved or suspended. The capsules are prepared by dip-coating or heat-melting methods.

The polymers that can be used in making the present hard capsule shells can be divided into the following groups: 1) Cellulose- or cellulose derived-based material, which include, but are not limited to, cellulose, cellulose ether, methyl cellulose, hydroxypropyl methyl cellulose, hydroxyprolyl cellulose, hydroxyethyl cellulose, carboxymethyl cellulose, cellulose acetate phthalate. 2) starch-based compounds, which include, but not limited to hydroxyethyl starch, hydroxypropyl starch, hydroxyethyl methyl starch, 3) carrageenans—kappa and iota, 4) Acrylate derivatives which include, but not limited to, polyacrylate, polymethylacrylate, poly(acrylate-methylacrylate), poly(methylacrylate-methyl methacrylate), 5) polyolefins which include, but limited to, polyvinyl chloride, polyvinyl alcohol, and polyvinyl acetate and 6) pullulan (a polysaccharide polymer consisting of maltotriose units).

DETAILED DESCRIPTION

A hard capsule dosage form is manufactured by filling the core of the hard capsule shell with powders, granules, beads, pellets, a tablet, another capsule or combination thereof. In the recent times, scientists have started to fill the hard capsule shells with liquids too. The hard capsule shells are purchased from the capsule suppliers. There are main three manufacturers of hard capsule shells—Capsugel, Shionogi and Universal Capsules. Each capsule has two parts—a body and a cap. Commonly used primary ingredients in the composition of the capsule body or the cap are gelatin and hydroxypropyl methyl cellulose. As mentioned in the earlier section, apart from gelatin, several new types of polymeric substances have been used to manufacture hard capsule shells. These are—cellulosic compounds, acrylates, starch ethers, polyolefins, pullulans, and carrageenans. Apart from the main constituent of the capsule shell, gelatin or polymer, the shell may also contain other excipients such as plasticizers (e.g., polyethylene glycol, sorbitol, glycerol), stabilizers (antimicrobial and antioxidants), colorants (FD&C colors, titanium dioxide, natural dyes including riboflavin, carotenes, turmeric and caramel) and sequestering agents (citric acid, sodium citrate, ethylenediaminetetraacetic acid).

The rate of capsule dissolution in a desired media governs the release of medicaments residing in the core of the capsule. The rate of release may be altered using selected combination of polymers in the capsule composition or by a cross-linking of gelatin or polymer used in the capsule shell formulation.

The present invention proposes a method to develop a combination dosage form in which the medicament resides in the core of the capsule and another in the hard capsule shell composition itself. The medicament in the hard capsule shell is either physically dispersed or molecularly dissolved or chemically bound to the gelatin or to the polymeric material of the capsule shell. In one embodiment, the body and the cap of the capsule shell contain the same active moiety. In another embodiment, either the cap or the body of the capsule shell contains the medicament. In yet another embodiment, different medicaments are incorporated in the body and the cap. In yet another embodiment, a combination of medicaments is incorporated in the body and cap of the hard capsule shell compositions.

According to the present invention, the hard capsule shell manufacturer will manufacture the capsule shell compositions containing a drug(s) and supply to a pharmaceutical company. The pharmaceutical company, purchasing the drug-loaded hard capsule shell compositions, will produce a suitable composition (such as powders, granules etc.) of the core material containing different drug(s) and fill it in the drug-loaded capsule shells.

There are various sizes of hard capsule shells available ranging from 000 to 5, the most commonly used are sizes 0 and 1. The fill weight of granules with a density of 0.7 g/mL is 475 mg and 350 mg for size 0 and 1 capsules, respectively. Size 000 capsule can contain 960 mg of core material loaded with medicament. The average weights of size 1 and 0 empty hard gelatin capsule shell are 75 mg and 98 mg, respectively. These weights can vary, but overall the weights are low. The drug loading in the capsule shell composition can affect the properties of the capsule shell; and thus, the amount of drug loaded in the capsule shell is limited. In general, only potent drugs can be loaded in capsule shells. Also, one skilled in the art will determine the stability of the drug in the capsule shell composition during manufacture and storage. It is important to establish the desired release rate of medicament from the capsule shell under pre-determined conditions such as in the acidic and basic media, and in the presence of bile acids/food etc. The polymer for the capsule shell and the drugs need to be selected judiciously.

Bioavailability of a drug constitutes of two features—the rate and the extent of absorption. For drugs with narrow therapeutic indices, it is critical to maintain appropriate drug levels in the blood or tissues. For potent drugs, one must avoid dumping of drugs in a short period from the delivery device into the gastro-intestinal tract so that one can avoid erratic blood levels of the medicament.

The medicament, if insoluble, forms a suspension in the capsule shell-forming composition. The medicament may dissolve in the capsule shell-forming composition and in some cases, the medicament may form an ion-pair bond with the groups in the polymer or the excipients used to prepare the capsule shell-forming composition. The medicament may form a covalent bond with the polymer or the excipients used to prepare the capsule composition. The chemical bond can be of any nature—peptide, an amide, an ester or other kinds.

Overall, the drug may be present in the capsule-shell formulation in three states—physically dispersed, molecularly dissolved and chemically bound or combination of these.

In one embodiment, the drug may be in partially physically dispersed and molecularly dissolved states in the capsule-shell composition. In another embodiment, the drug may be in partially physically dispersed and chemically bound states in the capsule shell composition. In yet another composition, the drug may be in partially molecularly dissolved and chemically bound states in the capsule-shell composition.

Upon administration of the hard shell capsule orally, it may disintegrate or dissolve in the mouth cavity releasing the drug (s). In another embodiment, the capsule shell may stay intact in the mouth cavity and may dissolve or disintegrate in the stomach releasing the drug(s). In another embodiment, the capsule shell may stay intact till it reaches the intestinal tract and may dissolve/disintegrate in the intestine releasing the drug(s).

The release of drug, which is embedded in the capsule shell composition, may be controlled by three mechanisms—diffusion through the shell matrix, hydrolysis of medicament-polymer chemical bond or by dissolution of the hard capsule shell to release the drug. In an embodiment, multiple drugs can be incorporated in the capsule shell composition, which could be released with different mechanisms. In another embodiment, a laminated hard shell capsule is prepared using the double pin-dip method. The drug-loaded polymer layer can be the inner or outer layer. One such type of lamination could be enteric coating. Enteric coating is a special coating that prevents release of the drug(s) from a dosage form until it reaches to the intestine.

Other medicaments may be placed in the capsule core in the form of powder, granules, beads, tablets, capsules etc. The concept can be more clear or evident with the following examples.

Example 1

Entecavir (0.5 mg) in the Gelatin Capsule Shell and Tenofovir (300 mg) in the Core for the Chronic Hepatitis B Treatment Entecavir and tenofovir are antiviral drugs used to treat hepatitis B. In a report by Petersen et al. (*J Hepatol.* 56(3):520-526, 2012), rescue therapy with entecavir and tenofovir in CHB patients harboring viral resistance patterns or showing only partial antiviral responses to preceding therapies was observed to be efficient, safe, and well tolerated in patients with and without advanced liver disease.

In an embodiment, Entecavir (0.5 mg) may be physically incorporated in size 0 hard gelatin capsule shell by mixing entecavir in the gelatin capsule shell-forming composition. The particle size distribution of entecavir will determine the dissolution rate of drug in the GI tract and thus, its absorption. Tenofovir pellets may be prepared using conventional methods and the pellets equivalent to 300 mg of active may be filled into the entercavir-loaded empty capsule shells.

Example 2

Clonidine (75 Microgram) in the Capsule Shell Composition and Bupivacaine (10 mg) in the Core for Labor Pain Polymer such as polymethacrylic acid (RCOOH) may be first converted to RCOCl form, which can react with clonidine in a suitable solvent system. The polymeric prodrug of clonidine may be dissolved in a suitable medium along with suitable excipients (plasticizer, coloring agent etc.) to form a solution. Hard capsule shells may be prepared using a pin-dip method known to those skilled in the art. Bupivacaine granules may be prepared using a conventional method and may be filled into the clonidine-loaded hard capsule shells. The dose of bupivacaine is 10 mg per capsule. Thus, in this case, bupivacaine may be released upon dissolution of hard capsule shell and clonidine may be released after the hydrolysis of amide bonds.

Example 3

Ethinyl Estradiol (30 Microgram) and Drosperenone (3 mg) in the Capsule Shell and Thalidomide (200 mg) in the Core Teratogens are drugs that can cause birth defects by interfering with the normal development of a fetus. Commonly known teratogens are—thalidomide, isotretinoin, tretinoin etc. If contraceptives are coadministered with these teratogens, women taking these drugs will prevent accidental pregnancy and thereby birth defects.

In this case, ethinyl estradiol bears a phenolic hydroxyl group, which can form an ester bond with RCOOH (for example, with carboxymethyl cellulose). The polymeric prodrug of ethinyl estradiol may be dissolved in an aqueous system along with necessary excipients for the capsule composition. Drospirenone has very low water solubility (1.8 mg/L water at 25° C.) and may be suspended in the capsule shell-forming solution and hard capsule shells are manufactured using the pin-dip method. Thalidomide granules may be prepared using a conventional technique. The granules may be filled in the ethinyl estradiol/drospirenone-loaded capsule shells to produce a combination dosage form.

Example 4

Omeprazole (10 mg) in the Capsule Shell and Pancrelipase (6000 to 24,000 USP Units of Lipase) in Core Hard gelatin capsule shells may be prepared with physically and molecularly distributing omeprazole (10 mg per capsule) in the capsule shell-forming composition, which may be further coated with cellulose acetate phthalate (enteric coating). Spheres of 1 to 2 mm diameter of pancrelipase may be prepared using conventional methods known to skilled in the art. For example, the spheres can be prepared using cetyl alcohol, dimethicone, polyethylene glycol and triethyl citrate. The spheres of pancrelipase may be filled in the omeprazole-loaded, enteric-coated hard capsule shells. Omeprazole and pancrelipase formulations are typically enteric coated due to rapid degradation in the acidic pH.

Example 5

Nabilone (1 mg) with Cyclophosphamide (50 mg)

In an embodiment, Nabilone, 1 mg, may be suspended in the gelatin capsule shell-forming composition. A chemotherapeutic agent, cyclophosphamide, 25 mg or 50 mg, granules may be prepared using suitable excipients and can be filled in the capsule shells with nabilone. Nabilone is a synthetic cannabinoid and has an excellent antiemetic property. Thus, it will reduce the nausea and vomiting caused by cyclophosphamide.

Other commonly used antiemetic agents such as, granisetron, ondansetron, metoclopramide etc. can be included in the capsule shell-forming composition. Several types of chemotherapeutic agents from classes including—Alkylating agents, Anthracyclines, Cytoskeletal disruptors (Taxanes), Epothilones, Histone Deacetylase Inhibitors, Inhibitors of Topoisomerase I, Inhibitors of Topoisomerase II, Kinase inhibitors, Monoclonal antibodies, Nucleotide analogs and precursor analogs, Peptide antibiotics, Platinum-based agents, Retinoids, and Vinca alkaloids and derivatives, which can be delivered in the capsule dosage form, and can be administered as a combination therapy using this platform.

Example 6

Naratriptan Hydrochloride (2.5 mg) in the Capsule Shell and Naproxen (500 mg) as the Core Material Naratriptan hydrochloride, 1 to 2.5 mg, is used to treat migraine. Naproxen is a known to be effective against pain and inflammation. Naratriptan hydrochloride may be dissolved in the HPMC or gelatin capsule shell-forming composition to produce naratriptan-loaded capsule shells. These capsules can be filled with the granules containing naproxen (normal dose is 500 mg). Naratriptan is sensitive to acidic and alkali degradations. A suitable buffering agent may be used in the capsule forming composition to maintain a neutral pH. Other triptans including almotriptan, eletriptan, rizatriptan and sumatriptan can also be used in the capsule shell-forming compositions.

Example 7

Probenecid, 500 mg as the Core Material and Colchicin, 0.5 mg in the Capsule Shell Composition Probenecid prevents tubular reabsorption of urates thereby increasing urinary excretion of uric acid. This way, probenecid can be used to prevent gout attacks. Colchicine is also used prevent gout attacks. Thus, Probenecid and colchicine combination is used to treat gout or gouty arthritis.

There is only one approved colchicine product in the US market (Colcrys, 0.6 mg by Takeda Pharma). Combination of probenecid and colchicine in the tablet dosage form are marketed by Watson (brand) and Mirror Pharma.

In an embodiment, colchicine, 0.5 mg may be incorporated in the hydroxyethyl starch capsule shell-forming composition. Colchicine solubility in water is 7 mg/mL. Hydroxyethyl starch is a biodegradable and water-soluble polysaccharide. Colchicine may be covalently bound to hydroxyethyl starch. The probenecid granules can be filled in these colchicine-loaded empty capsule shells.

Example 8

Vitamin B12 in the Capsule Shell and Metformin in the Capsule Core

Almost 30% of people taking metformin face vitamin B12 deficiency. In another embodiment, Vitamin B12 may be dissolved in the HPMC or gelatin capsule shell-forming composition. These Vitamin B12-loaded capsule shells may be filled with metformin granules. Such a combination will prevent Vitamin B12 deficiency in any patients taking metformin.

Example 9

Pramipexole Dihydrochloride (0.25 mg) in the Capsule Shell Composition and Sertraline (50 mg) as the Core Material Pramipexole is known primarily for treating schizophrenia and particularly for the treatment of Parkinson's disease. In the U.S. Pat. No. 6,255,329, a much better antidepressant activity was observed when pramipexole was combined with another antidepressant agent. Sertraline was one of the antidepressant agent chosen. Other antidepressant may be used with pramipexole could be alprazolam, chlordiazepoxide, clomipramine, chinpirol, dibenzepin, doxepin, fluvoxamine, lofepramine, maprotiline, mirtazapine, mianserin, moclobemide, nefazodone, nortriptyline, opipramol, paroxetine, sulpiride, tranylcypromine, trazodone, trimipramine, tryptophan, venlafaxine and viloxazine. The patent described the following dosage forms for the delivery of such combinations—plain or coated tablets, lozenges, powders, solutions, suspensions, emulsions, syrups, suppositories etc.

In this example, pramipexole dihydrochloride, 0.25 mg, may be dissolved in the capsule shell-forming composition, which can be converted to pramipexole-loaded empty capsule shells. Sertraline, 50 mg, granules may be filled in these pramipexole-loaded empty capsule shells.

From the foregoing, it is clear that this patent application opens up several possibilities using the drug-loaded hard capsule shell as a carrier of different medicaments along with a different set of drugs in the core. While specific embodiments have been presented here, various modifications can be made and the invention is not limited to the examples shown in this patent application.

In conclusion, this patent application teaches to incorporate medicament(s), physically distributed, molecularly dissolved and/or chemically bound into the matrix of the capsule shell composition. The base capsule matrix consists of gelatin or a suitable polymeric material along with other excipients. This capsule shell composition is used to prepare the body and cap of the empty capsule shell. When put together, the body and the cap produce the empty capsule shell. When a drug is loaded in the body and the cap or both of the capsule shell composition, it forms a drug-loaded empty capsule shell. The inside region of the drug-loaded empty capsule shell is hollow and it is defined as the "core" of the empty capsule shell. The word "empty" signifies that the core of the drug-loaded empty capsule shell has nothing inside, when the drug-loaded empty shell capsule manufacturer sells to its customers. Other medicaments in the form of drug-loaded matrices (e.g., powders, granules, pellets, mini-tablets and mini-capsules) may be filled in the core of these drug-loaded empty capsule shells. In some cases, nothing is filled in the core of these drug-loaded empty capsule shells. In some cases, a placebo matrix can be filled in these drug-loaded capsule shells too.

One can incorporate one drug in the cap or in the body of the capsule shell compositions. One can incorporate the same drug both in the cap and body of the capsule shell compositions. In another instance, one can incorporate one drug in the cap and second drug in the body of the capsule shell compositions. The release of medicaments incorporated in the capsule shell composition or medicaments filled inside the capsule shell core can be modified by inner and out laminations or by entering coating of capsule shell.

The invention claimed is:

1. A hard shell capsule comprising:
    a body and a cap cooperatively defining a hollow core hard shell capsule;
    each of the body and cap comprising a composition, at least one of the body composition and the cap composition comprising a therapeutically effective amount of a drug(s) loaded throughout said at least one of the body composition and the cap composition;
    wherein the capsule has an inner laminate layer or an outer laminate layer or an inner and an outer laminate layer.

2. The hard shell capsule of claim 1 wherein the drug(s) is physically dispersed throughout said at least one of the body and the cap composition.

3. The hard shell capsule of claim 1 wherein the drug(s) is molecularly dissolved throughout said at least one of the body and the cap composition.

4. The hard shell capsule of claim 1 wherein the drug(s) is chemically bonded with said at least one of the body and the cap composition.

5. The hard shell capsule of claim 1 wherein the drug(s) is at least one of (a), (b), and (c): (a) partially physically dispersed throughout said at least one of the body and cap compositions, (b) partially chemically bonded with the said at least one of the body and cap compositions, and (c) is partially molecularly dissolved in said at least one of the body and cap compositions.

6. The hard shell capsule of claim 1 wherein the drug(s) are present throughout the cap and the body compositions and at least a portion of the drug(s) is molecularly dissolved in the cap and the body compositions.

7. The hard shell capsule of claim 1 having no other drug in the capsule core.

8. The hard shell capsule of claim 1 wherein the said at least one of the cap composition and the body composition comprises at least one of the following: gelatin, hydroxypropylmethyl cellulose, and carrageenan.

9. The hard shell capsule of claim 1 wherein the drug(s) is present in both the cap composition and the body composition, and the same drug(s) is present in the cap composition as is present in the body composition.

10. The hard shell capsule of claim 1 wherein the drug(s) is present in both the cap composition and the body composition, and the drug(s) present in the cap composition is different from the drug(s) present in the body composition.

11. A hard shell capsule comprising:
    a body and a cap cooperatively defining a hollow core hard shell capsule;
    each of the body and cap comprising a composition, at least one of the body and the cap comprising a therapeutically effective amount of a drug(s) loaded throughout the composition of the said at least one of the body and the cap;
    wherein the body and cap composition comprises a polymer, the drug(s) being chemically bonded with the polymer of the said at least one of the body and the cap.

12. The hard shell capsule of claim 11 wherein the polymer of the body and cap composition comprises at least one of the following: gelatin, hydroxypropylmethyl cellulose, and carrageenan.

13. The hard shell capsule of claim 11 having no other drug in the capsule core.

14. A hard shell capsule comprising:
    a body, a cap, a therapeutically effective amount of a drug(s); each of the body and cap comprising a composition, the body and the cap cooperatively defining a hollow core hard shell capsule; and the drug(s) being present throughout the cap and the body compositions,
    wherein one or both of the cap and the body compositions comprises a polymer, at least a portion of the drug(s) being chemically bonded with the polymer.

15. The hard shell capsule of claim 14 wherein the cap and body each comprise an enteric coating.

16. The hard shell capsule of claim 14 wherein the polymer of the one or both of the body and the cap compositions comprises at least one of the following: gelatin, hydroxypropylmethyl cellulose, and carrageenan.

17. The hard shell capsule of claim 14 having no other drug in the capsule core.

18. The hard shell capsule of claim 14 wherein a first portion of the drug(s) is chemically bonded with the polymer and a second portion of the drug is not chemically bonded with the polymer.

19. The hard shell capsule of claim 14 wherein the same drug(s) is present in the cap composition as is present in the body composition.

20. The hard shell capsule of claim 14 wherein the drug(s) present in the cap composition is different from the drug(s) present in the body composition.

* * * * *